US012583881B2

(12) United States Patent
Tadino et al.

(10) Patent No.: US 12,583,881 B2
(45) Date of Patent: *Mar. 24, 2026

(54) DEVICE AND CASSETTE FOR PERFORMING A PLURALITY OF SYNTHESIS PROCESSES OF PREPARING A RADIOPHARMACEUTICAL IN SERIES

(71) Applicant: OUT AND OUT CHEMISTRY S.P.R.L., Neuville (BE)

(72) Inventors: Vincent Luc Antoine Tadino, Chastres (BE); Guillaume André René Villeret, Dimont (FR)

(73) Assignee: OUT AND OUT CHEMISTRY S.P.R.L., Neuville (BE)

( * ) Notice: Subject to any disclaimer, the term of this patent is extended or adjusted under 35 U.S.C. 154(b) by 5 days.

This patent is subject to a terminal disclaimer.

(21) Appl. No.: 18/493,909

(22) Filed: Oct. 25, 2023

(65) Prior Publication Data

US 2024/0059724 A1 Feb. 22, 2024

Related U.S. Application Data

(60) Continuation of application No. 16/424,677, filed on May 29, 2019, now Pat. No. 11,820,790, which is a division of application No. 15/570,771, filed as application No. PCT/EP2016/061319 on May 19, 2016, now Pat. No. 10,344,045.

(30) Foreign Application Priority Data

May 20, 2015 (NL) ...................................... 2014828

(51) Int. Cl.
| | |
|---|---|
| C07H 5/02 | (2006.01) |
| B01J 19/24 | (2006.01) |
| B01J 41/00 | (2006.01) |
| C01D 3/02 | (2006.01) |
| C07B 59/00 | (2006.01) |
| C07C 39/40 | (2006.01) |
| C07C 53/18 | (2006.01) |
| C07C 215/40 | (2006.01) |
| C07C 229/36 | (2006.01) |
| C07D 207/46 | (2006.01) |
| C07D 233/91 | (2006.01) |
| C07H 1/06 | (2006.01) |
| C07H 19/06 | (2006.01) |

(52) U.S. Cl.
CPC .............. *C07H 5/02* (2013.01); *B01J 19/24* (2013.01); *B01J 41/00* (2013.01); *C01D 3/02* (2013.01); *C07B 59/00* (2013.01); *C07C 39/40* (2013.01); *C07C 53/18* (2013.01); *C07C 215/40* (2013.01); *C07C 229/36* (2013.01); *C07D 207/46* (2013.01); *C07D 233/91* (2013.01); *C07H 19/06* (2013.01); *B01J 2219/24* (2013.01); *C07C 2603/40* (2017.05)

(58) Field of Classification Search
CPC .. C07H 5/02; C07H 1/06; C07B 59/00; C07D 207/45
See application file for complete search history.

(56) References Cited

U.S. PATENT DOCUMENTS

| | | | |
|---|---|---|---|
| 2,191,853 A | 2/1940 | Holmes | |
| 7,586,102 B2 | 9/2009 | Mourtada et al. | |
| 10,703,771 B2 | 7/2020 | Franci et al. | |
| 2004/0022696 A1* | 2/2004 | Zigler ................ | G01N 35/1079 |
| | | | 422/159 |
| 2011/0150714 A1 | 6/2011 | Elizarov et al. | |
| 2011/0184159 A1 | 7/2011 | Friebe et al. | |
| 2011/0305618 A1 | 12/2011 | Graham et al. | |

(Continued)

FOREIGN PATENT DOCUMENTS

| | | |
|---|---|---|
| BE | 895821 A | 5/1983 |
| CA | 2795762 A | 10/2011 |

(Continued)

OTHER PUBLICATIONS

Mark Lazari et al. Fully Automated Production of Diverse 18F-Labeled PET Tracerson the ELIXYS Multir eactor Radiosynthesizer With out Hard ware Modification, J Nucl Med Technol, 42, 203-210. (Year: 2014).*

Francesco De Leonardis et al., On-Chip pre-concentration and complexation of [18F]fluoride ions via regenarble anion exchange particles for radiochemical synthesis of Positron Emission Tomography tracers, J Chromatography A, 1218, 4714-4719. (Year: 2011).*

Bashir, Mohammed J.K., et al., Recycling of the exhausted cation exchange resin for stabilized landfill leachate treatment, ResearchGate, Conference Paper, The 4" International Engineering Conference Towards engineering of 21" century, Oct. 2012, pp. 1-12.

Bhandare, Rajendra Bhaskar, Ion Exchangers as Catalyst in Esterification Reaction: A Review, International Journal of Chemical Engineering Research. ISSN 0975-6442 vol. 10, No. 2 (2018), pp. 105-118.

(Continued)

*Primary Examiner* — Michael G. Hartley
*Assistant Examiner* — Jagadishwar R Samala
(74) *Attorney, Agent, or Firm* — Hoffmann & Baron, LLP

(57) ABSTRACT

A method of performing a plurality of synthesis processes of preparing a radiopharmaceutical in series, which method includes carrying out a first synthesis run comprising the steps of: a) providing water containing 18F; b) trapping the 18F from the water provided in step a) on an anion exchange material; c) eluting the trapped 18F from the anion exchange material to a reaction vessel of first radiopharmaceutical synthesis cassette; d) preparing a radiopharmaceutical incorporating the eluted 18F using the first radiopharmaceutical synthesis cassette; where steps a)-d) are repeated in at least one subsequent run using another radiopharmaceutical synthesis cassette; and where the method includes a reconditioning step of treating the anion exchange material with water between two consecutive runs. Other aspects of the invention relate to a device for performing this method, and a cassette for use in the device.

7 Claims, 3 Drawing Sheets

(56) References Cited

U.S. PATENT DOCUMENTS

| | | | |
|---|---|---|---|
| 2013/0102772 A1 | 4/2013 | Eshima et al. | |
| 2013/0324715 A1 | 12/2013 | Wickstrom et al. | |
| 2014/0213757 A1 | 7/2014 | Shales | |
| 2015/0165074 A1 | 6/2015 | Lazewatsky et al. | |
| 2017/0320901 A1 | 11/2017 | Franci et al. | |

FOREIGN PATENT DOCUMENTS

| | | | | |
|---|---|---|---|---|
| CN | 1765911 | A | 5/2006 | |
| CN | 101104627 | A | 1/2008 | |
| CN | 101333138 | A | 12/2008 | |
| EP | 949632 | A2 | 10/1999 | |
| EP | 2110367 | A1 * | 10/2009 | ............ C07B 59/00 |
| JP | 2005-3603 | A | 1/2005 | |
| KR | 10-2011-0106895 | A | 9/2011 | |
| KR | 10-2013-0132892 | A | 12/2013 | |
| WO | WO 02/101758 | A1 | 12/2002 | |
| WO | WO 2006/119226 | A2 | 11/2006 | |
| WO | WO 2010/003548 | A1 | 1/2010 | |
| WO | WO 2011/097649 | A2 | 8/2011 | |
| WO | WO 2011/141410 | A1 | 11/2011 | |
| WO | WO 2012/083094 | A1 | 6/2012 | |
| WO | WO 2013/127439 | A1 | 9/2013 | |
| WO | WO 2013/188459 | A2 | 12/2013 | |
| WO | WO 2014/018419 | A1 | 1/2014 | |
| WO | WO 2015/071288 | A1 | 5/2015 | |

OTHER PUBLICATIONS

C. Lemaire et al., "Fast [18F]FDG synthesis by alkaline hydrolysis on a low polarity solid phase support"; Journal of Labelled Compounds and Radiopharmaceuticals, vol. 45, Issue 5, Apr. 2002, pp. 435-447.

Cai, Lisheng, et al., Chemistry with [18F]Fluoride Ion, MICROREVIEW, Eur. I Org. Chem., 2008, pp. 2853-2873.

Chu, Y.E., et al., Design of a Fluorine-18 Production System at ORNL Cyclotronn Facility, Part 2, Oak Ridge National Laboratory, Nov. 28, 1977, pp. 1-23.

CN Office Action, Application No. 201680028939.6, May 15, 2020, 16 pages (w/translation).

CN Search Report, Application No. 2016800289396, May 9, 2020, 4 pages (w/translation).

Culbert, P.A., et al., Automated Synthesis of [18F]FDG using Tetrabutylammonium Bicarbonate, Appl. Radiat. Isot. vol. 46, No. 9, pp. 887-891, 1995.

Cyclotron Produced Radionuclides: Guidance on Facility Design and Production of[ 18F]Fluorodeoxyglucose (FDG); Applied Radiation and Isotopes, vol. 68, Issue 9, Sep. 2010, pp. 1-153.

De Leonardis, Francesco et al., On-chip pre-concentration and complexation of [18F]fluoride ions via regenerable anion exchange particles for radiochemical synthesis of .Positron Emission Tomography tracers, doi: 10.1016/j.chroma.2011.05.062 (2011), pp. 4714-4719.

Desilva, Frank, Resin Regeneration Fundamentals, Regeneration procedures and guidelines for softeners and two-bed deionizers, Water Quality Products, Apr. 1, 2006, pp. 1-9.

DOWEX Ion Exchange Resins, Water Conditioning Manual, Dow Water Solutions, pp. 1-93, Apr. 13, 2016.

Extemporaneous Preparation of Radiopharmaceuticals, European Pharmacopoeia 11.0, Apr. 2022, pp. 849-854.

Fadzil, Muhammad Fakhrurazi Ahmad et al., Upgrades and regulatory aspects of [18F] Fluorodeoxyglucose ([18F]FDG) production using the FASTLab2 synthesizer, Journal of Radioanalytical and Nuclear Chemistry (2022) 331:99-110.

Francesco De Leonardis et al., "On-chip pre-concentration and complexation of [18F]fluoride ions via regenerable anion exchange particles for radiochemical synthesis of Positron Emission Tomography tracers"; Journal of Chromatography A, vol. 1218, Issue 29, Jul. 22, 2011, pp. 4714-4719.

Gomzina, N.A., et al., Optimization of Automated Synthesis of 2-[18F]Fluoro-2-deoxy-D-glucose Involving Base Hydrolysis, Radiochemistry, vol. 44, No. 4, 2002, pp. 403-409.

Gozmina N.A et al al., Optimization of Automated Synthesis of 2-[18F]Fluoro-2-deoxy-D-glucose Involving Base Hydrolysis, Radiochemistry, vol. 44. No. 4, 2002, pp. 366-372.

Hamacher, et al., Efficient Stereospecific Synthesis of No-Carrier-Added 2-[18F]-Fluoro-2-DeoxyD-Glucose Using Aminopolyether Supported Nucleophilic Substitution, J Nucl Med 27:235-238, 1986.

Hidekazu Saiki et al., "Electrochemical concentration of No. carrier-added [18F]fluoride from [18O]water in a disposable microfluidic cell for radiosynthesis of 18F-labeled radiopharmaceuticals"; Applied Radiation and Isotopes, vol. 68, Issue 9, Sep. 2010, pp. 1703-1708.

Hjelstuen, Ole K., et al, Standardization of fluorine-18 manufacturing processes: New scientific challenges for PET, European Journal of Pharmaceutics and Biopharmaceutics 78 (2011) pp. 307-313.

IN Office Action, Application No. 20172704357, Apr. 24, 2020, 6 pages.

International Search Report for corresponding International Application No. PCT/EP2016/061319, filed on May 19, 2016, mailed Jul. 18, 2016, 3 pages.

International Written Opinion for corresponding International Application No. PCT/EP2016/061319, filed on May 19, 2016, mailed Jul. 18, 2016, 5 pages.

Ion Exchange Resins: What They Are and Their Applications, excedr, https://www.excedr.com/resources/ion-exchange-resins-what-they-are-and-their-applications/, Jul. 26, 2022, pp. 1-8.

Iwata, Ren et al., A concentration-based microscale method for 18F-nucleophilic substitutions and its testing on the one-pot radiosynthesis of [18F]FET and [18F] fallypride, Applied Radiation and Isotopes 166 (2020) 109361; http://www.elsevier.com/locate/apradiso; 7 pp.

Jewett, Douglas M., Aqueous Carbonic Acid: a Readily Removable Electrolyte for the Recovery of [18F] Fluoride from Anion Exchange Resins, Appl. Radiat. Isol. vol. 42. No. 4, 1991, Int. J. Radiat. Appl. Instrum., Part A, pp. 410-411.

Johansson, Bo-Lennart, et al., Column lifetime of a new agarose medium for high-performance gel filtration chromatography at basic pH, Journal of Chromatography, 330 (1985) Elsevier Science Publishers B.V., Amsterdam, Netherlands, pp. 360-364.

Kilian, Krzysztof, et al., Synthesis, quality control and determination of metallic impurities in 18F-fludeoxyglucose production process, Reports of Practical Oncology and Radiotherapy 19 (2014) S22-S31, Greater Poland Cancer Centre. Published by Elsevier Urban & Partner Sp. z o.o.

Lazari, Mark et al. "Fully Automated Production of Diverse 18F-Labeled PET Tracers on the ELIXYS Multireactor Radiosynthesizer Without Hardware Modification," Downloaded from tech.snmjournals.org on Oct. 23, 2018, pp. 203-211.

Lazari, Mark et al., Fully Automated Production of Diverse 18F-Labeled PET Tracers on the ELIXYS Radiosynthesizer Without Hardware Modification, Journal of Nuclear Medicine Technology, Sep. 2014, vol. 42, No. 3, pp. 203-210.

Lebedev, Artem, et al., Batch-reactor microfluidic device: first human use of a microfluidically produced PET radiotracer. Lab Chip. Jan. 7, 2013; 13(1): 136-145. doi: 10.1039/c2lc40853h, 23 pp.

Lemaire, C. et al., Fast [18F ]FDG synthesis by alkaline hydrolysis on a low polarity solid phase support, Journal of Labelled Compounds and Radiopharmaceuticals, J Label Compd Radiopharm 2002; 45: 435-447.

Link, J. M. et al., Sources of carrier F-19 in F-18 fluoride, AIP Conference Proceedings 1509, 61 (2012); https://doi.org/10.1063/1.4773941, 6 pp.

Liu, Zhibo et al., One-step 18F labeling of biomolecules using organotrifluoroborates, NatProtoc. Sep. 2015 ; 10(9): 1423-1432, 26 pp.

Myers, Robert J. et al., Synthetic Resins as Exchange Adsorbents, Industrial and Engineering Chemistry, vol. 33, No. 6, 1941, pp. 697-706.

Myers, Robert J., et al., Synthetic Resins as Exchange Adsorbents, Industrial and Engineering Chemistry vol. 33, No. 6, Jun. 1941, pp. 697-706.

(56) References Cited

OTHER PUBLICATIONS

Netherlands Search Report and Written Opinion for corresponding NL Application No. 2014828, dated Jan. 7, 2016, 9 pages.

Norling, Lenore, et al., Impact of multiple re-use of anion-exchange chromatography media on virus removal, Journal of Chromatography A, 1069 (2005) pp. 79-89.

Salvador, Blas, et al., Disposable PDMS Chip With Integrated [18F]Fluoride Pre-Concentration Cartridge for Radiopharmaceuticals, Journal of Microelectromechanical Systems, vol. 26, No. 6, Dec. 2017, pp. 1442-1448.

Sample Preparation, http://www.waters.com/sampleprep, 42 pp.

Schlyer, David J. et al., Separation of [18F]Fluoride ion from [180]Water Using Anion Exchange Cartridge, Applied Radiation and Isotopes, vol. 41, No. 6, 1990, pp. 531-533.

Schlyer, David J., Separation of [18F]Fluoride from [180]Water Using Anion Exchange Resin, Int. J. Radiat. Appl. Instrum. Part A, Appl. Radiat. Isot. vol. 41, No. 6, pp. 531-533, 1990, Great Britain.

Schubiger, P.A. et al., PET Chemistry, The Driving Force in Molecular Imaging, Ersnt Schering Research Foundation, Workshop 62, Springer, 2007, pp. 292-294.

Schueller, Michael John, et al., Separating long-lived metal ions from18F during H218O recovery, Nuclear Instruments and Methods in Physics Research B 261 (2007), pp. 795-799.

Sep-Pak Accell Plus QMA Plus Light Cartridge, 130 mg Sorbent per Cartridge, 37-55 µm, 50/pk, Waters, Feb. 16, 23, pp. 1-6.

Third Party Observations, Korean Patent Application No. 10-2017-7036762, Oct. 7, 2022, 22 pages.

Wang, Jia et al., Multi-GBq production of the radiotracer [18F]fallypride in a droplet microreactor, Royal Society of Chemistry, RSC Adv., Oct. 2020, pp. 7828-7838.

Wang, Jia et al., Supplemental Information: Multi-GBq Production of the Radiotracer [18F] Fallypride in a Droplet Microreactor, The Royal Society of Chemistry 2020, RSC Adv., pp. 1-17.

Waters AccellPlus QMA and CM Bulk Media, Care and Use Manual, Waters, Dec. 2012, pp. 1-5.

Waters The Science of What's Possible, Care and Use Manual, Waters AccellPlus QMA and CM Bulk Media, Dec. 2012, 5 pages. https://www.waters.com/waters/support.htm?locale=104&lid=134716347&cid=511442&type=USRM.

Wheaton, R.M. et al., Fundamentals of Ion Exchange, Dow Chemical USA, Jun. 2000, 9 pages.

Wheaton, R.M., Dow Liquid Separations, DOWEX, Ion Exchange Resins, Fundamentals of Ion Exchange, Dow Chemical U.S.A., Jun. 2000, pp. 1-9.

De Leonardis et al., Journal of Chromatography A 1218 (2011):4714-4719.†

Liu et al., Nature Protocols 2015; 10(9): 1423-1432.†

Lazari et al., J. Nucl Med Technol 2014; 42:203-210.†

\* cited by examiner
† cited by third party

DEVICE AND CASSETTE FOR PERFORMING A PLURALITY OF SYNTHESIS PROCESSES OF PREPARING A RADIOPHARMACEUTICAL IN SERIES

CROSS-REFERENCE TO RELATED APPLICATIONS

This application is a continuation of U.S. application Ser. No. 16/424,677, filed May 29, 2019, which is divisional of U.S. application Ser. No. 15/570,771, filed Oct. 31, 2017, now U.S. Pat. No. 10,344,045, granted Jul. 9, 2019, which is the National Stage of International Application No. PCT/EP2016/061319 filed May 19, 2016, which claims the benefit of Netherlands Application No. NL 2014828, filed May 20, 2015, the contents of all of which are incorporated by reference herein.

FIELD OF THE INVENTION

The invention relates to a method of performing a plurality of synthesis processes of preparing a radiopharmaceutical in series, a device for performing this method and a cassette for use in the method.

BACKGROUND OF THE INVENTION

Radioisotopes for PET (Positron Emission Tomography) are generally produced using a cyclotron. In the cyclotron charged particles are accelerated thereby gaining energy. Upon exiting the cyclotron the accelerated particles hit a target thereby producing positron emitters. Fluorine-18 (hereinafter 18F) is produced by proton bombardment of oxygen-18 water ($H_2^{18}O$). The proton interacts with the 18O and produces a neutron and 18F. The thus produced 18F is allowed to react with a suitable starting material, thereby producing an appropriate tracer (radiopharmaceutical) for diagnosis purposes such as cancer and brain disorders.

Many synthetic routes to prepare PET radiopharmaceuticals have been developed during recent decades. The great majority of PET tracers are labelled with the positron-emitting radioisotopes 11C and 18F (radioactivity decay: half-lives of 20 and 110 min, respectively). For 18F based radiopharmaceuticals production two preparation methods have been developed and used throughout the world, electrophilic and nucleophilic 18F fluorination. These reactions are usually performed in a so called synthesizer. Today commercially available synthesizers are highly automated devices for the production of the tracer, wherein the direct involvement of operating staff and exposure to radiation is reduced in order to protect them against radiation.

After irradiation the produced 18F in a 18O enriched water solution is usually passed to an anion exchange material, where the 18F is trapped. The 18O water is collected. Subsequently the 18F is eluted using typically an eluent like $K_2CO_3$. K18F is not soluble in organic solvents that are suitable for performing the subsequent nucleophilic reaction steps. Therefore a so called phase transfer agent is also added. Typical examples thereof include tetra alkyl ammonium salts or aminopolyethers, like Kryptofix®. As fluoride is reactive in water-free media only, any remaining water is usually removed in one or more evaporation steps, typically using dry acetonitrile under a flow of inert gas like helium or nitrogen. The 18F once dried and solubilised in the presence of the phase transfer agent is ready for the main nucleophilic substitution steps. In the production of 18F-FDG (F-18 fluoro-2-deoxyglucose) typically a precursor is added like mannose triflate. This compound has a triflate group as a suitable leaving group, while the acetyl groups ensure that fluorination only occurs at the position of the triflate group. This reaction step is usually carried out at elevated temperature like 80-90° C. In the next step the protective acetyl groups are removed by hydrolysis. Both basic hydrolysis typically using NaOH and acid hydrolysis using HCl can be employed. Basic hydrolysis has the advantage that it can be carried out at room temperature in a short time interval, whereas acid hydrolysis frequently requires a substantial higher temperature and lasts longer. Finally the thus produced 18F-FDG is purified, which is commonly performed using several purification steps using different chromatographic materials.

The synthesizers used can be classified into two categories. A first category comprises stationary systems without any removable components. All connections, tubing, valves, vessels are permanently installed. After completion of a production run, the components are rinsed in a CIP (Clean-In-Place) operation. Although this kind of synthesizers is said to have the advantage of cost savings due to reusing its components, complete cleaning and sterilization may be difficult to achieve. Moreover, a full CIP operation may be lengthy, resulting in a serious downtime of the synthesizer. Additionally waste volumes resulting from the CIP operation may be relatively high. Also a cleaning operation may lead to a drop of labelling yield. Typically such a stationary system is dedicated to the production of a single radiopharmaceutical, because its configuration cannot be easily adapted to allow production of another tracer.

A second category comprises synthesizers which are based on the use of removable kits or cassettes. In some cassettes the reagents need to be activated prior to use. Other cassettes are ready-to-use and need only to be inserted. All process steps including prior testing sequences and related process parameters and other data are predetermined and part of the software, which is installed in a suitable programmable logical controller (PLC), server or PC. Each synthesizer has its own PC, router and PLC, or customized electronic board. Principally cassette based synthesizers are useful for performing subsequent syntheses, which depending on the selected cassette, reagents kits and software may produce different radiopharmaceuticals.

In view of radiation protection (radio-safety) synthesizers are installed in a so called hot cell, a protective shielding typically made from lead. The size and amount of shielding is mainly dependent on the dimensions and configuration of the synthesizer. Thus compactness of the synthesizer is highly desirable in view of costs and weight of the shielding. After a production run, the device contains still radioactive residues, so that manually handling the synthesizer is dangerous. Decay periods of more than 12 hours are likely to be observed, before the residual activity on the spent cassette has dropped below a certain limit and the synthesizer can be accessed safely. This is a serious drawback if multiple batches are to be produced during a single day.

Several approaches to solve these issues are known from the prior art.

E.g. WO 2012/083094 A1 discloses that performing two back-to-back synthesis runs of fluciclatide in quick succession on two different cassettes is technically difficult due to the residual activity, to which the operator would be exposed during spent-cassette dismounting procedures. In order to shield the operating staff from this residual activity on the cartridge during the short time required for this dismounting procedure it is proposed in this document to provide a shielding collar specific for a separation cartridge used on the synthesis cassette.

WO 2006/119226 A2 has disclosed an apparatus and method for making radiopharmaceuticals, which synthesizer comprises a stationary processor having a disposable kit interface planar structure, a plurality of rotary actuators and push-on fluidic connectors protruding from this interface, structure for releasably interfacing a disposable kit to the actuators and connectors, and associated disposable kit. Linear actuators translate the kit toward and after processing from supports on the processor, so that the kit can fall in a suitable container.

One way of preparing multiple batches of radiopharmaceuticals, which may be the same or different, is providing a number, e.g. four, of synthesizers in one or more hot cells, each synthesizer being controlled with its own dedicated computer, PLC and so forth, including waste containers. Such a setup is spacious and expensive in view of shielding and equipment.

SUMMARY OF THE INVENTION

The invention aims at providing a method and device for performing a plurality of synthesizing processes of preparing batches of one or more radiopharmaceuticals in series, of which the expenses in equipment are reduced, while ensuring minimal involvement of operating staff and relatively short downtime.

Another object of the invention is to provide such a method and synthesizer allowing an economical waste management.

According to the invention a method of performing a plurality of synthesis processes of preparing a radiopharmaceutical in series comprises carrying out a first synthesis run comprising the steps of:
  a) providing water containing 18F;
  b) trapping the 18F from the water provided in step a) on an anion exchange material;
  c) eluting the trapped 18F from the anion exchange material to a reaction vessel of a first radiopharmaceutical synthesis cassette;
  d) preparing a radiopharmaceutical incorporating the eluted 18F using the first radiopharmaceutical synthesis cassette;
  wherein steps a)-d) are repeated in at least one subsequent run using another radiopharmaceutical synthesis cassette; and
  wherein the method comprises a reconditioning step of said anion exchange material between two consecutive runs.

In the method according to the invention a series of consecutive batchwise synthesis processes of preparing a radiopharmaceutical is performed using different radiopharmaceutical synthesis cassettes, except for the trapping of 18F supplied from the target, on an anion-exchanger and subsequent elution thereof. These trapping and elution steps are carried out using the same anion-exchanger material and associated equipment for each synthesis of the series. Between subsequent runs the anion-exchanger is reconditioned. It has been discovered that reconditioning of the anion-exchanger can be performed rather easily, while maintaining its trapping capacity and without cross-contamination occurring. The method according to the invention allows to install the equipment and chemicals for trapping, elution and reconditioning, preferably as a cassette, as well as the various cassettes for the synthesis runs, which may be the same or different, in one time in a synthesizer, and to perform the various subsequent synthesis runs without the need of accessing the hot cell, thereby avoiding the operator being exposed to residual activity. Thus the subsequent runs are independent and do not need a full CIP operation or cleaning of a spent cassette. A main advantage is that the series of processes can be controlled using a single server, router and PLC. Another important advantage is related to waste management. A single recovery bottle for 18O water suffices, as well as a single waste bottle for the reconditioning solutions used for reconditioning the anion-exchanger. The waste liquids resulting from the subsequent synthesis runs can be collected in a single waste bottle as well. Compared to the amount of waste produced upon a full CIP operation, the volume of the spent reconditioning liquids is small in the method according to the invention. This is beneficial in view of waste management. Furthermore as the actual 18F labelling synthesis itself is carried out each time on a fresh cassette, labelling yield does not suffer from deterioration due to repeatedly cleaning. In addition reuse of the anion exchanging material reduces the costs of the series of synthesis reactions.

In the context of this application a cassette comprises the radiopharmaceutical synthesis process specific hardware components and chemicals required for performing the respective synthesis. For example, such a radiopharmaceutical synthesis cassette comprises one or more manifolds provided with suitable valves that can be operated by a synthesizer, having a plurality of connections such as luer connectors, tubing, one or more reaction vessel(s) and vials containing the necessary reagents and other liquids, optionally separation and/or purification cartridges. Suitably the vials containing the necessary reagents and other liquids may be obtained as a separate kit of chemicals, while the other hardware components of the cassette are obtained as a pre-mounted assembly.

The design of the method also allows to use a compact synthesizer. E.g. a synthesizer for performing the method according to the invention producing three subsequent batches of 18F-FDG can be installed in a small space having dimensions (width×height×depth) of 560 mm×420 mm×360 mm.

A preferred anion exchange material comprises a quaternary ammonium anion exchange material, in particular quaternary methyl ammonium (QMA), such as the silica-based ion exchanger cartridges loaded with QMA, e.g. Sep-Pak® Accell Plus QMA Plus Light Cartridge available from Waters Corporation, or Chromafix® PS-HCO3 available from MACHEREY-NAGEL GmbH & Co. KG. These QMA cartridges can be easily reconditioned using a carbonate solution. The carbonate concentration has appeared not very critical. A suitable concentration is in the range of 0.01-5 M. For example, both a 1M and a 0.05 M $K_2CO_3$ solution have proven to allow successful reconditioning. In a preferred embodiment the carbonate solution is prepared in situ by diluting a concentrated carbonate solution with water allowing to reduce the dimensions of the container (bottle) for the carbonate solution. E.g. a 1M $K_2CO_3$ solution can be easily diluted with water for injection in the trapping, elution and reconditioning cassette by suitable operation.

A rinsing operation comprising one or more rinsing steps with only pure water can be used for reconditioning QMA as anion exchange material. However, pure water will not remove the metallic impurities derived from the target and also trapped on the QMA, and these impurities maybe released by the eluent in a next elution step. Thus, using pure water may cause cross-contamination between subsequent runs.

It is also possible to regenerate the anion exchange material with the preferred eluent mixture itself (discussed hereinbelow), but due to the low carbonate concentration thereof, the volume required for reconditioning will be higher than with a carbonate solution having a higher concentration as exemplified above. The use of the preferred eluent mixture also as a reconditioning agent for reconditioning the anion exchange material will additionally result in waste of the expensive crown ether (=phase transfer agent).

It is possible to elute the trapped 18F from the anion-exchanger using only an aqueous carbonate solution. Ammonia in water works as well. Suitably, in these cases a phase transfer agent is added to the reaction vessel in the synthesis cassette. Preferably the phase transfer agent is a crown ether like Kryptofix® 2.2.2., or a tetra alkyl ammonium salt. More preferably, the eluent is a mixture comprising carbonate, phase transfer agent, water and acetonitrile.

A suitable example comprises a mixture of 0.7-7 mg of $K_2CO_3$, 0.3-1 mL of $CH_3CN$, 5-30 mg of Kryptofix® 2.2.2. in 0.1-0.5 mL of $H_2O$. Here the amount of potassium carbonate can be replaced by $Me_xH_yCO_3$ wherein Me represents an alkali metal and x is 1-2 and x+y=2, such as $Li_2CO_3$, $Cs_2CO_3$, $NaHCO_3$, $KHCO_3$. Another suitable mixture is composed of 75 mM $nBU_4NHCO_3$, 750 μL $H_2O$, EtOH (stabilizer).

In this way the phase transfer agent and organic solvent like acetonitrile for drying do not need to be part of the synthesis cassettes used for the actual production of the radiopharmaceutical in question.

The method according to the invention can be used for a variety of radiopharmaceuticals based on 18F.

Examples include

18F-FDG ([18F]-fluoro-2-deoxyglucose),

FMISO (1-(2-nitro-imidazolyl)-3-[18F]-fluoro-2-propanol; 1H-1-(3-[18F]-fluoro-2-hydroxypropyl)-2-nitro-imidazole), NaF (sodium [18F]-fluoride), 18F-FLT (3'-deoxy-3'-[18F] fluoro thymidine):

18F-FET (0-(2-[18F]-fluoro ethyl)-L-tyrosine)

18F-FES (16 α-[18F]fluoro-17 β-estradiol),

FCHOL ([18F] fluorocholine)

FACETATE ([18F] fluoroacetate)

FDGal ([18F] fluorodeoxygalactose)

F DOPA (L-6-[18F] fluoro-3,4-dihydroxyphenylalanine)

18SFB (N-succinimidyl 4-[18F]fluorobenzoate).

Production of 18F-FDG is a preferred synthesis process.

As described hereinbefore, the subsequent synthesis runs can be directed to the preparation of radiopharmaceuticals, which may be the same or different. In a preferred embodiment all subsequent synthesis runs produce the same radiopharmaceutical.

According to a second aspect the invention provides a device for performing a plurality of synthesis processes of preparing a radiopharmaceutical in series, in particular as explained above, comprising a frame or housing an inlet for introducing water containing 18F;

an anion-exchanger comprising an anionic exchange material connected to said inlet;

an eluent container comprising an eluent connected to said anion-exchanger;

a recondition container comprising a reconditioning agent connected to said anion-exchanger, distribution means for selectively supplying eluted 18F to a radiopharmaceutical synthesis cassette;

at least two radiopharmaceutical synthesis cassettes, each cassette being connected to said distribution means.

The frame or housing has the function of providing a structure for mounting the other components, in particular the necessary tubes and other conduits including valves and actuators thereof, the reagents and waste containers and cassettes. The radiopharmaceutical synthesis cassettes are as described above.

In a preferred embodiment thereof in the device according to the invention the components, reagents necessary for trapping 18F, elution thereof and reconditioning of the anionic exchange material are contained in a ready-to-use cassette.

Advantageously the device according to the invention comprises a single server loaded with suitable software, router and PLC for inputting and selecting processes and controlling the device.

According to a third aspect the invention also provides a cassette for use in the device according to the invention, which cassette comprises at least one manifold provided with a plurality of valves connectable to and operable by the device according to the invention an anion-exchanger comprising an anionic exchange material;

an eluent container comprising an eluent a recondition container comprising a reconditioning agent.

The anion-exchanger, eluent container and recondition container are connectable to the at least one manifold.

In a preferred embodiment thereof the recondition container contains a concentrated carbonate solution, and the cassette also is provided with a container comprising water.

The advantages as explained above with respect to the method according to the invention are applicable in a similar way to the device and cassette according to the invention.

BRIEF DESCRIPTION OF THE DRAWINGS

The invention will be illustrated by reference to the attached drawings, wherein.

DETAILED DESCRIPTION OF THE INVENTION

Figure 1:
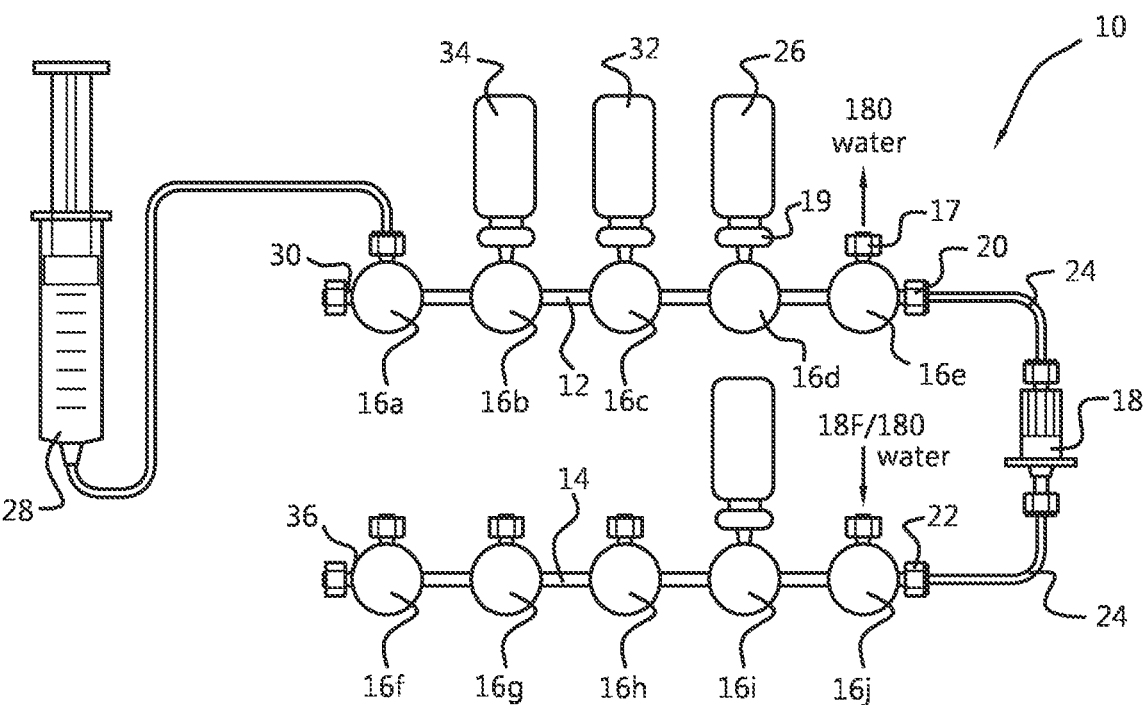
FIG. 1 shows a diagrammatic view of a part of a synthesizer, in particular a cassette suitable for trapping 18F, eluting and reconditioning.

In FIG. 1 a part of a synthesizer being an embodiment of a disposable reconditioning cassette according to the invention, for trapping 18F on an anionic exchange material, subsequent elution and reconditioning of the anion exchange material, is shown diagrammatically. In the embodiment shown the cassette indicated in its entirety by reference numeral 10, comprises a first manifold 12 and a second manifold 14. Each manifold 12, 14 comprises five 3 way valves 16, individually indicated 16a through 16e, and 16f-16j respectively. These reference numerals are also used to indicate the respective positions. The valves 16 are preferably operated by compressed air as disclosed in WO 2013/127439 A1, which is incorporated by reference. Typically connections with tubing occurs by luerlock connectors 17, while (reagent) vials and other bottles are usually closed by suitable septums 19 that are spiked.

Water containing 18F is derived from a cyclotron (not shown) and introduced at 16j and trapped on anion-exchanger 18, such as a Sep-Pak Accell Plus QMA Carbonate Plus Light cartridge available from Waters Corporation, which is connected to the right hand ends 20, 22 of manifolds 12 and 14 via tubing 24. The water is removed at 16e and collected into a bottle or other container (not shown). Once the 18F is trapped by anion-exchanger 18 an eluent, typically a mixture of (potassium) carbonate, a transfer agent like Kryptofix, water and acetonitrile, from vial 26 is metered in syringe 28 via valves 16d, 16a and then passed over the anion-exchanger 18 thereby extracting the 18F and sending it to a reaction vessel of one of the synthesis cassettes (see FIG. 3) at valves 16f-h. The left end 30 of manifold 12 is connected to a source of an inert gas such as nitrogen or helium.

For reconditioning the anion-exchanger 18 reconditioning agent, typically an aqueous carbonate solution, is used. In the embodiment shown in FIG. 1, this solution is prepared in situ in syringe 28 from a high molar K₂CO₃ solution in vial 32 at position 16c and water from bottle 34 at position 16b. It will be recognized that the vials 26, 32, 34 can be placed in any order. Then the diluted K₂CO₃ solution thus prepared is ejected from syringe 28 over anion-exchanger 18 to a waste bottle (not shown) connected to the left hand end 36 at position 16f of manifold 14. Subsequently one or more rinsing steps are carried out with water from bottle 34 using syringe 28. The spent water is collected in the same waste bottle at 36. The anion-exchanger 18 is dried using the inert gas introduced at 30. The water at 16i is used for each synthesis step requiring water, that is to say water is sampled from 16i for subsequent synthesis runs. Cross-contamination is not possible because the water arrives from 16 f g h in the different runs.

Figure 2:
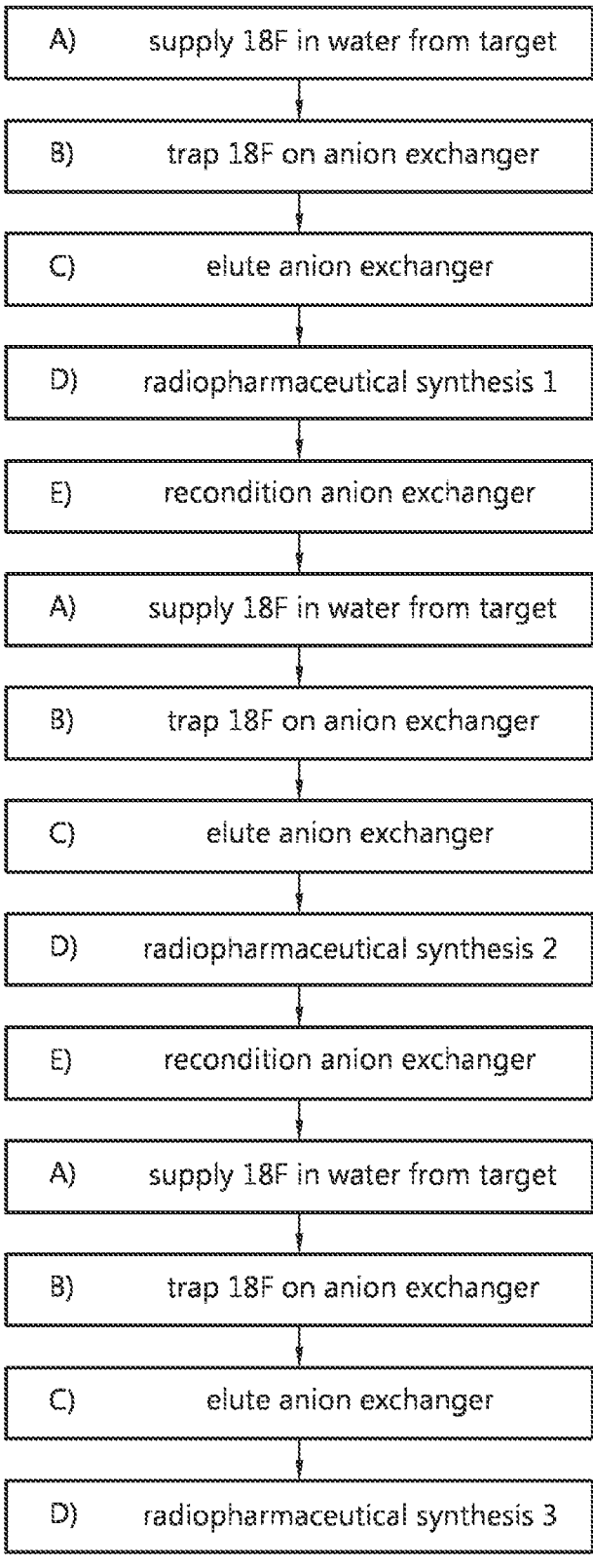
FIG. 2 shows an example of a process scheme for performing a number of synthesis processes according to the invention.

FIG. 2 shows an example of a process scheme for performing multiple reactions in series.

The series of reactions start with supply of 18F in water from a target and trapping thereof on the anion-exchanger. Then the trapped 18F is eluted to radiopharmaceutical synthesis process 1. The anion-exchanger is reconditioned. Thereafter the sequence of steps A) through D) is repeated using the same anion-exchanger, but the eluted 18F is now guided to a second synthesis process 2. Upon finishing this synthesis process, the anion-exchanger is reconditioned once more, and the sequence of steps A) through D) is repeated for the last time.

Figure 3:
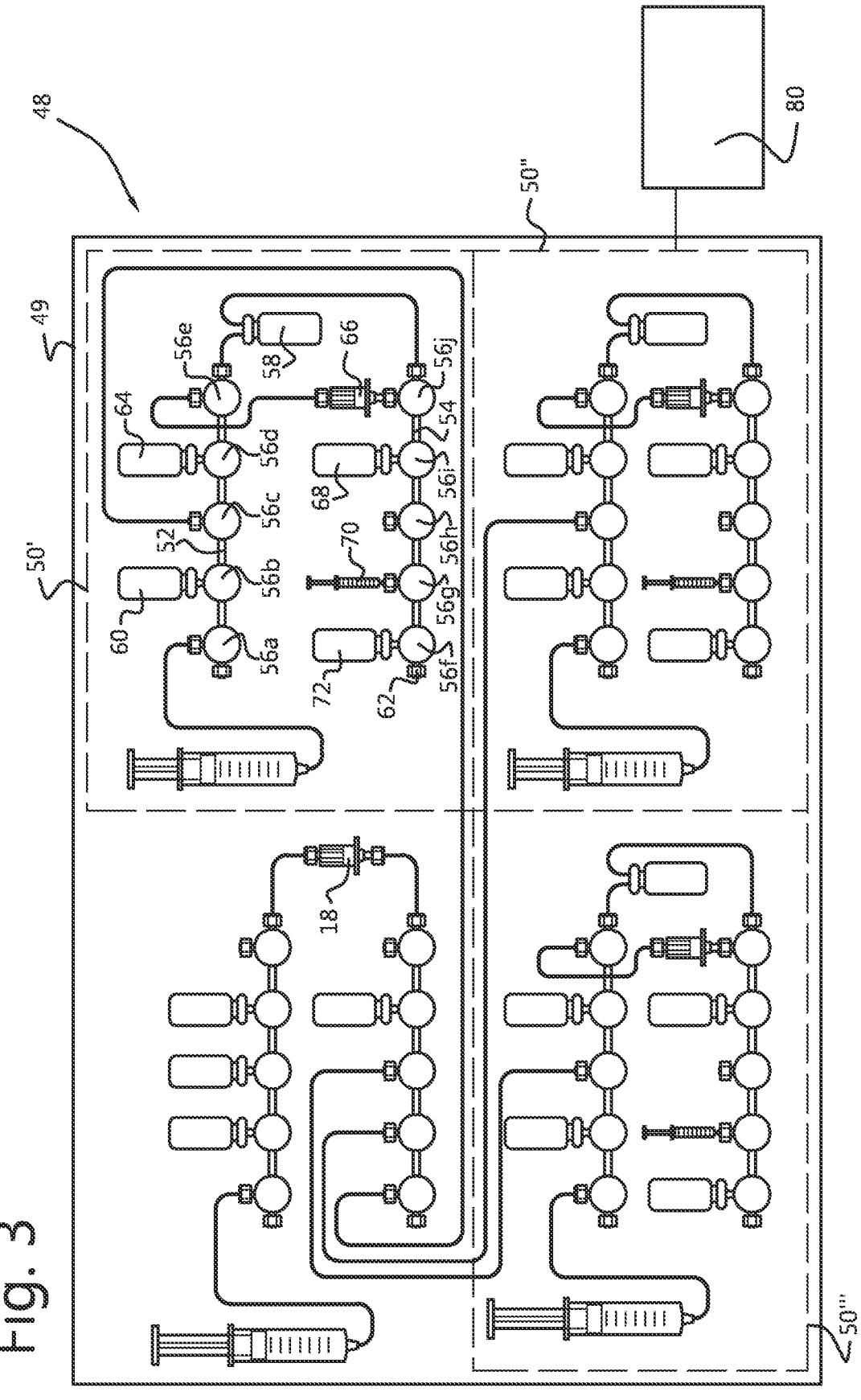
FIG. 3 shows a diagrammatic view of a synthesizer for performing a number of synthesis processes according to the invention.

FIG. 3 shows an embodiment of a synthesizer 48 having a frame or housing 49 allowing insertion of cassettes, wherein 3 consecutive batches of 18F-FDG are prepared using—in this embodiment—identical radiopharmaceutical synthesis cassettes 50 (diagrammatically shown in broken lines). Each cassette comprises two manifold 52 and 54, and each manifold has five 3 way valves 56 (or positions), numbered 56a-e and 56f-j respectively. In the top left part of the synthesizer the eluent mixture containing 18F is prepared as explained above with reference to FIG. 1. This eluent mixture is used in the first synthesis process of 18F-FDG. The eluent mixture is introduced in a cassette 50' at position 56c and collected in reactor vessel 58, which can be heated by heating means (not shown). Therein the eluent mixture comprising 18F is dried using acetonitrile from bottle 60. Waste is collected at left hand end 62 of manifold 54. Precursor is added from vial 64 at position 56d. After reaction the thus produced intermediate product, after dilution with water sampled in 16i is separated on a suitable solid phase extraction cartridge 66 at position 56j and eluted back into the reaction vessel 58 using a suitable eluent such as EtOH from vial 68 at position 56i. If the chemistry allows so, the water container or bag may be incorporated in the radiopharmaceutical synthesis cassette 50, 50' or 50". The protective groups of the intermediate product are removed by means of basic hydrolysis using NaOH contained in syringe 70 at position 56g. The final product after buffering with buffer from vial 72 at position 56f is removed via valve 56h for subsequent formulation and quality control. After approval it can be used for diagnosis purposes. The syringe on position 56a is used for the pressurization of vials 60, 64, 72, 68, and for sampling of chemicals solutions, for dilution of reactive bulk mixture, and loading of the separation cartridges.

After this first production run the reconditioning of the anion-exchanger 18 is performed as outlined above with respect to FIG. 1. Fresh 18F containing water is again trapped on the thus reconditioned anion exchanger 18 and subsequently eluted to the second synthesis process cassette 50", where 18F-FDG is produced in the same way as described with respect to cassette 50'. Also after this second production run reconditioning of the anion-exchanger takes place. Then a third batch of eluent mixture containing 18F is prepared and used in synthesis process 3 in cassette 50'''.

The synthesizer 48 is operated by a single control system 80 comprising PLC, router and server (PC).

In an embodiment of the synthesizer 48 the cassette 10 and cassettes 50', 50" and 50' are releasably mounted on a fixed upright front plate of the frame or housing 49, while common pumps, drivers and other electronics and the like are mounted on a detachable upright rear plate (not visible in FIG. 3). For example the rear plate is connected to the frame or housing 49 using removable hinges, that are horizontally arranged at the bottom. For access to the components on the rear plate it is rotated backwards over a certain angle allowing inspection, servicing and maintenance of the components, while hooks or other connecting elements maintain the rear plate in this inclined position. Upon detachment of these hooks, the rear plate can rotate further down to an essentially horizontal position. In this position the rear plate can be removed as a module from the synthesizer.

The invention claimed is:

1. A method of performing a plurality of synthesis processes of preparing a radiopharmaceutical in series, which method comprises carrying out a first synthesis run comprising the steps of:
  a) providing water containing 18F;
  b) trapping the 18F from the water provided in step a) on an anion exchange material;
  c) eluting the trapped 18F from the anion exchange material to a reaction vessel of a first radiopharmaceutical synthesis cassette;
  d) preparing a radiopharmaceutical incorporating the eluted 18F using the first radiopharmaceutical synthesis cassette;
  wherein steps a)-d) are repeated in at least one subsequent run using another radiopharmaceutical synthesis cassette; and
  wherein the method comprises a reconditioning step of said anion exchange material between two consecutive runs, said reconditioning step comprises treating the anion exchange material with water.

2. The method according to claim 1, wherein said anion exchange material is a quaternary ammonium anion exchange material.

3. The method according to claim 1, wherein in step c) the eluent comprises a phase transfer agent.

4. The method according to claim 1, wherein the radio-pharmaceutical is selected from the group consisting of FDG, FMISO, NaF, FLT, FET, FES, FCHOL, FACETATE, FDGal, FDOPA, and SFB.

5. The method according to claim 1, wherein at least one process of said plurality of synthesis processes comprises preparing 18FDG.

6. The method of claim 1, wherein said reconditioning step comprises treating the anion exchange material with pure water.

7. The method of claim 1, wherein said reconditioning step comprises treating the anion exchange material with only water.

* * * * *